United States Patent
Biedermann et al.

(10) Patent No.: US 7,833,256 B2
(45) Date of Patent: Nov. 16, 2010

(54) ELASTIC ELEMENT FOR THE USE IN A STABILIZATION DEVICE FOR BONES AND VERTEBRAE AND METHOD FOR THE MANUFACTURE OF SUCH ELASTIC ELEMENT

(75) Inventors: Lutz Biedermann, VS-Villingen (DE); Jürgen Harms, Karlsruhe (DE); Wilfried Matthis, Weisweil (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 0 days.

(21) Appl. No.: 11/102,247

(22) Filed: Apr. 8, 2005

(65) Prior Publication Data
US 2006/0129147 A1 Jun. 15, 2006

Related U.S. Application Data
(60) Provisional application No. 60/563,241, filed on Apr. 16, 2004.

(30) Foreign Application Priority Data
Apr. 16, 2004 (DE) ................. 10 2004 018 621

(51) Int. Cl.
*A61B 17/84* (2006.01)
(52) U.S. Cl. ..................... 606/300
(58) Field of Classification Search ............ 606/60–61, 606/254–258, 279, 304; 623/17.13; 267/166, 267/168; 29/2.25
See application file for complete search history.

(56) References Cited

U.S. PATENT DOCUMENTS

| | | | |
|---|---|---|---|
| 5,236,169 A | * | 8/1993 | Johnsen ................. 248/561 |
| 5,306,310 A | | 4/1994 | Siebels ................... 623/17 |
| 5,423,816 A | * | 6/1995 | Lin ....................... 606/61 |
| 5,423,817 A | * | 6/1995 | Lin ....................... 606/61 |
| 5,488,761 A | * | 2/1996 | Leone ................... 29/2.25 |
| 5,500,122 A | | 3/1996 | Schwartz |

(Continued)

FOREIGN PATENT DOCUMENTS

DE 41 18 303 A1 1/1992

(Continued)

OTHER PUBLICATIONS

European Search Report dated Jul. 13, 2005 for application No. EP 05 00 8060.

(Continued)

*Primary Examiner*—Thomas C Barrett
*Assistant Examiner*—Michael J Araj
(74) *Attorney, Agent, or Firm*—Christie, Parker & Hale LLP

(57) ABSTRACT

A stabilization device for bones or vertebrae includes a substantially cylindrical elastic element. The elastic element has a first end and a second end opposite to the first end. An elastic section extends between the first end and the second end. The elastic section includes at least first and second helical coils. The first and second helical coils are arranged coaxially so that the first helical coil extends at least in a portion between the second helical coil. The elastic element may form, for example, a portion of a rod, bone anchoring element, or plate.

27 Claims, 14 Drawing Sheets

U.S. PATENT DOCUMENTS

| | | | |
|---|---|---|---|
| 5,551,674 A * | 9/1996 | Johnsen | 267/168 |
| 5,944,302 A | 8/1999 | Loc et al. | |
| 6,162,223 A | 12/2000 | Orsak et al. | 606/59 |
| 6,197,065 B1 | 3/2001 | Martin et al. | 623/23.17 |
| 6,656,184 B1 * | 12/2003 | White et al. | 606/73 |
| 6,986,771 B2 | 1/2006 | Paul et al. | |
| 2003/0030204 A1 * | 2/2003 | Chou | 267/177 |
| 2003/0109880 A1 | 6/2003 | Shirado et al. | 606/61 |
| 2003/0191470 A1 | 10/2003 | Ritland | 606/61 |
| 2003/0220643 A1 | 11/2003 | Ferree | 606/61 |
| 2004/0073218 A1 | 4/2004 | Dahners | |
| 2004/0082953 A1 | 4/2004 | Petit | |
| 2004/0147929 A1 * | 7/2004 | Biedermann et al. | 606/61 |
| 2004/0236327 A1 | 11/2004 | Paul et al. | |
| 2004/0236328 A1 | 11/2004 | Paul et al. | |
| 2005/0056979 A1 | 3/2005 | Studer et al. | |
| 2005/0154390 A1 * | 7/2005 | Biedermann et al. | 606/61 |

FOREIGN PATENT DOCUMENTS

| | | |
|---|---|---|
| EP | 0 529 275 A2 | 3/1993 |
| GB | 2 382 304 | 5/2003 |
| JP | 7-49082 | 2/1995 |
| WO | WO 02/09625 A1 | 2/2002 |
| WO | WO 03/047442 A1 | 6/2003 |
| WO | WO 2004/105577 A2 | 12/2004 |

OTHER PUBLICATIONS

European Search Report for parallel application EP 09 01 4615, dated Feb. 16, 2010, 8 pages.

* cited by examiner

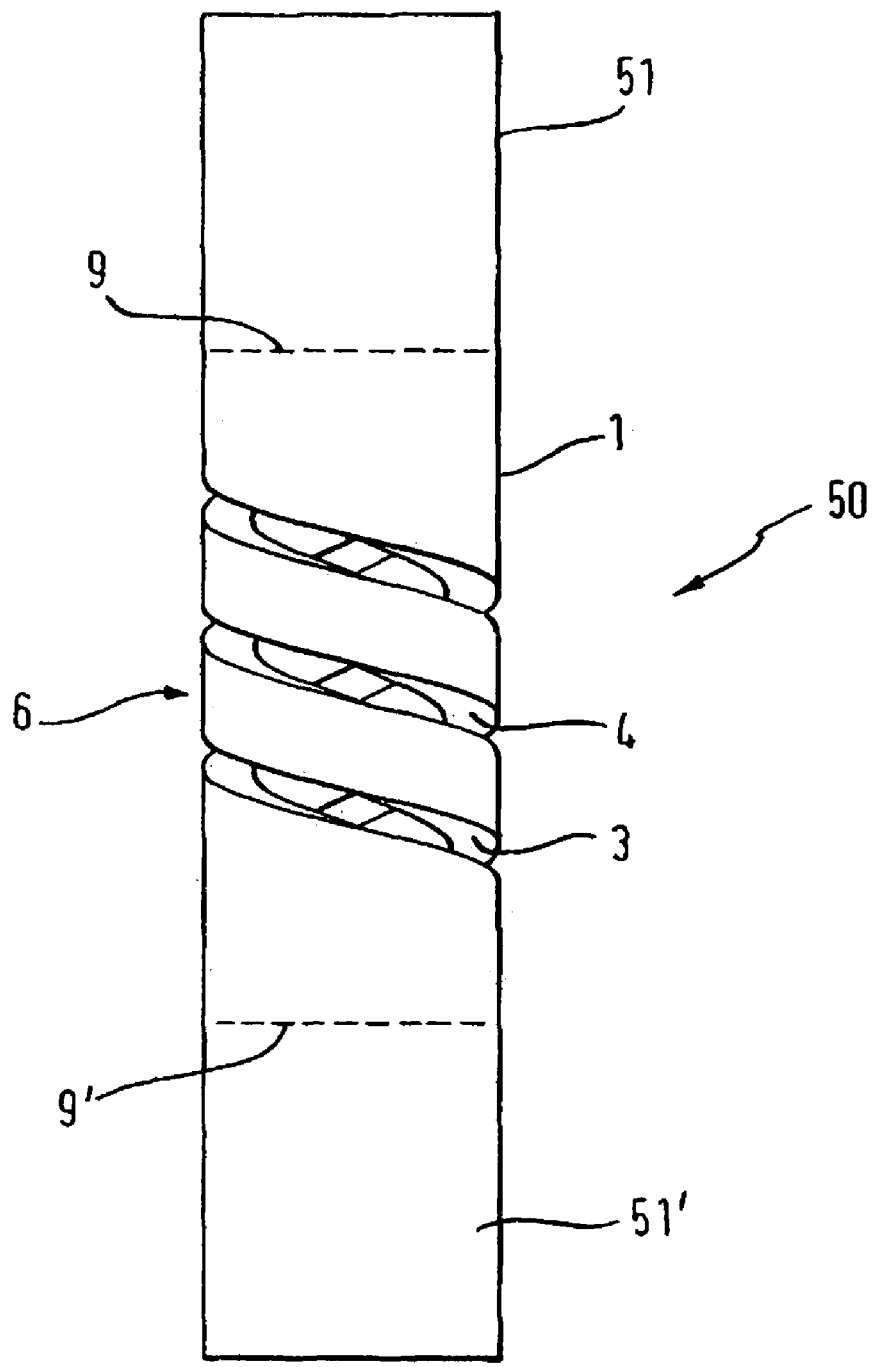

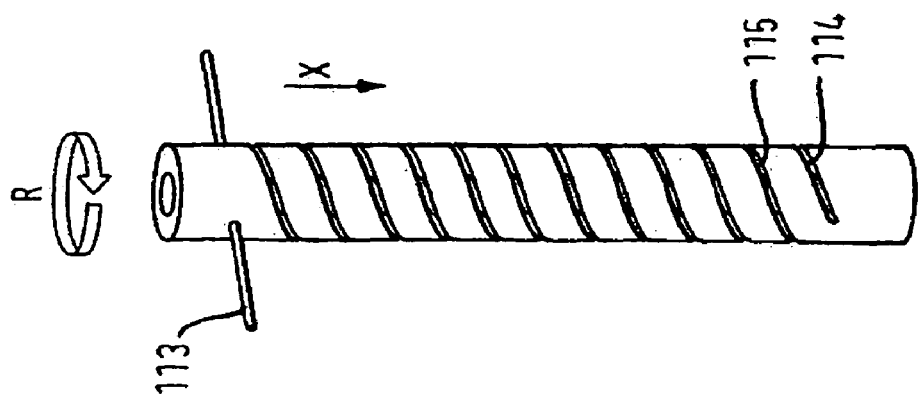
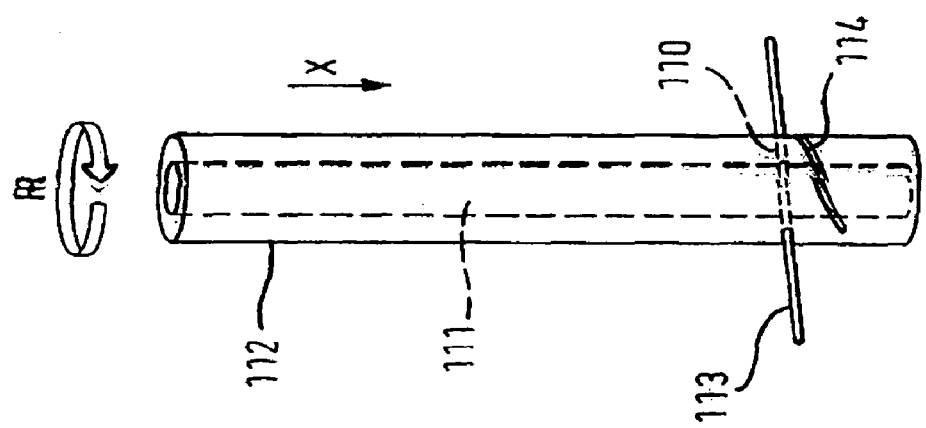
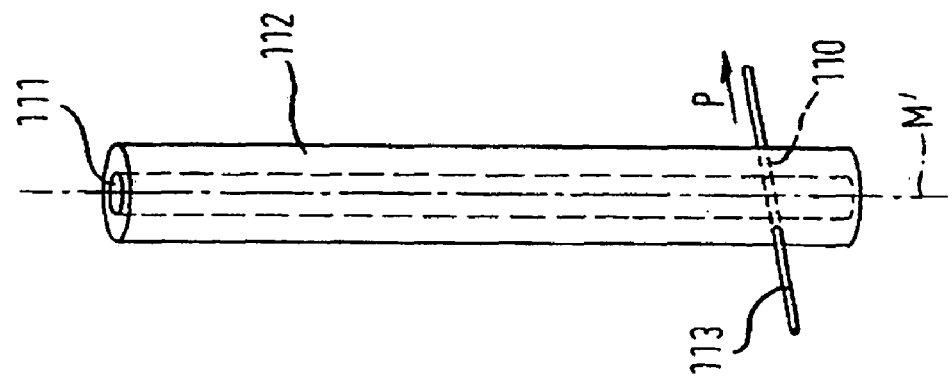

US 7,833,256 B2

ELASTIC ELEMENT FOR THE USE IN A STABILIZATION DEVICE FOR BONES AND VERTEBRAE AND METHOD FOR THE MANUFACTURE OF SUCH ELASTIC ELEMENT

REFERENCE TO EARLIER FILED APPLICATIONS

The present invention claims the benefit of the filing date under 35 U.S.C. §119(e) of U.S. Provisional Patent Application Ser. No. 60/563,241, filed Apr. 16, 2004, which is hereby incorporated by reference. The present application also claims foreign priority benefits pursuant to 35 U.S.C. §119 (a-d) for German Patent Application Number 10 2004 018 621.9, filed Apr. 16, 2004 in Germany.

BACKGROUND

The present invention relates to an elastic element for use in a bone anchoring element, a connecting element, a rod, and a stabilization device and a method for manufacturing the same.

It is known to use fixation and stabilization devices to fix fractures and stabilize spinal columns. These fixation and stabilization devices commonly comprise at least two bone anchoring elements or bone screws. Each of the bone anchoring elements is anchored in a bone or vertebra and is connected by a rigid plate or a rod. These types of fixation and stabilization devices generally do not allow any movement of the bones or vertebrae relative to each other.

In some instances, however, it is desirable to stabilize the bones or vertebrae so that the bones or vertebrae can carry out limited, controlled motion relative to each other. This is known as dynamic stabilization. Dynamic stabilization devices commonly comprise an elastic element instead of a rigid plate or rod that connects each of the bone anchoring elements.

One example of a dynamic stabilization device for vertebra is disclosed in United States Patent Application Publication No. 2003/0109880 A1. The dynamic stabilization device comprises first and second screws that are each anchored in a vertebra. Each of the screws has a receiving member for insertion of a spring which thereby connects the screws. The spring is provided in the form of a helical spring having closely neighboring coils like a tension spring. The spring is fixed in the receiving members by clamping screws. In this arrangement, however, because the spring is flexible, the spring can evade the pressure of the clamping screw and therefore become unfixed from the bone screw. Furthermore, both the elasticity and the flexural strength of the spring depend on the length of the spring. Thus, in applications requiring a spring with a short length, the elasticity and flexural strength of the spring is relatively small.

Another example of a dynamic stabilization device for a joint such as a wrist or knee joint is disclosed in U.S. Pat. No. 6,162,223. The dynamic stabilization device comprises a rod having a proximal rod section and a distal rod section connected to bone pins. The proximal rod section and the distal rod section are connected to each other by a flexible spring. The proximal rod section, the distal rod section, and the flexible spring are arranged outside of the body. The proximal rod section and the distal rod section are not fixedly connected to the flexible spring, but can move freely along a bore therein. In this arrangement, the flexible spring must be formed to have a diameter larger than a diameter of the rod. Additionally, the flexible spring must be large in order to have a high flexural strength. This dynamic stabilization device therefore has a complicated and voluminous structure, which prevents the dynamic stabilization device from being used inside the body on spinal columns.

BRIEF SUMMARY

The invention relates to an elastic element for use in a stabilization device for bones or vertebrae. The elastic element comprises a substantially cylindrical member having a first end, a second end opposite to the first end, and an elastic section between the first end and the second end. The elastic section includes at least first and second helical coils. The first and second helical coils are arranged coaxially so that the first helical coil extends at least in a portion between the second helical coil.

The invention further relates to a stabilization device for bones or vertebrae comprising a substantially cylindrical elastic element. The elastic element has a first end and a second end opposite to the first end. At least one of the first and second ends has threads. An elastic section extends between the first end and the second end. The elastic section includes at least first and second helical coils. The first and second helical coils are arranged coaxially so that the first helical coil extends at least in a portion between the second helical coil.

The invention still further relates to a method of manufacturing an elastic element for a stabilization device for bones or vertebrae. The method includes providing a substantially cylindrical body and forming first and second helical recess in the cylindrical body from an outside so that the first helical recesses are formed at least in a portion between the second helical recesses.

BRIEF DESCRIPTION OF THE DRAWINGS

FIG. 4b is a partial exploded view of the elastic element of FIG. 4a;

FIG. 5b is a sectional view of the elastic element of FIG. 5a;

FIG. 7b is a sectional view of the elastic element of FIG. 7a

FIG. 8a is a elevational view of a rod comprising the elastic element of FIG. 1;

FIG. 10a is a schematic illustration of a method of manufacturing the elastic element of FIG. 1;

FIG. 10b is a schematic illustration of a method of manufacturing the elastic element of FIG. 1;

FIG. 10c is a schematic illustration of a method of manufacturing the elastic element of FIG. 1.

DETAILED DESCRIPTION OF THE DRAWINGS AND PRESENTLY PREFERRED EMBODIMENTS

Figure 1:
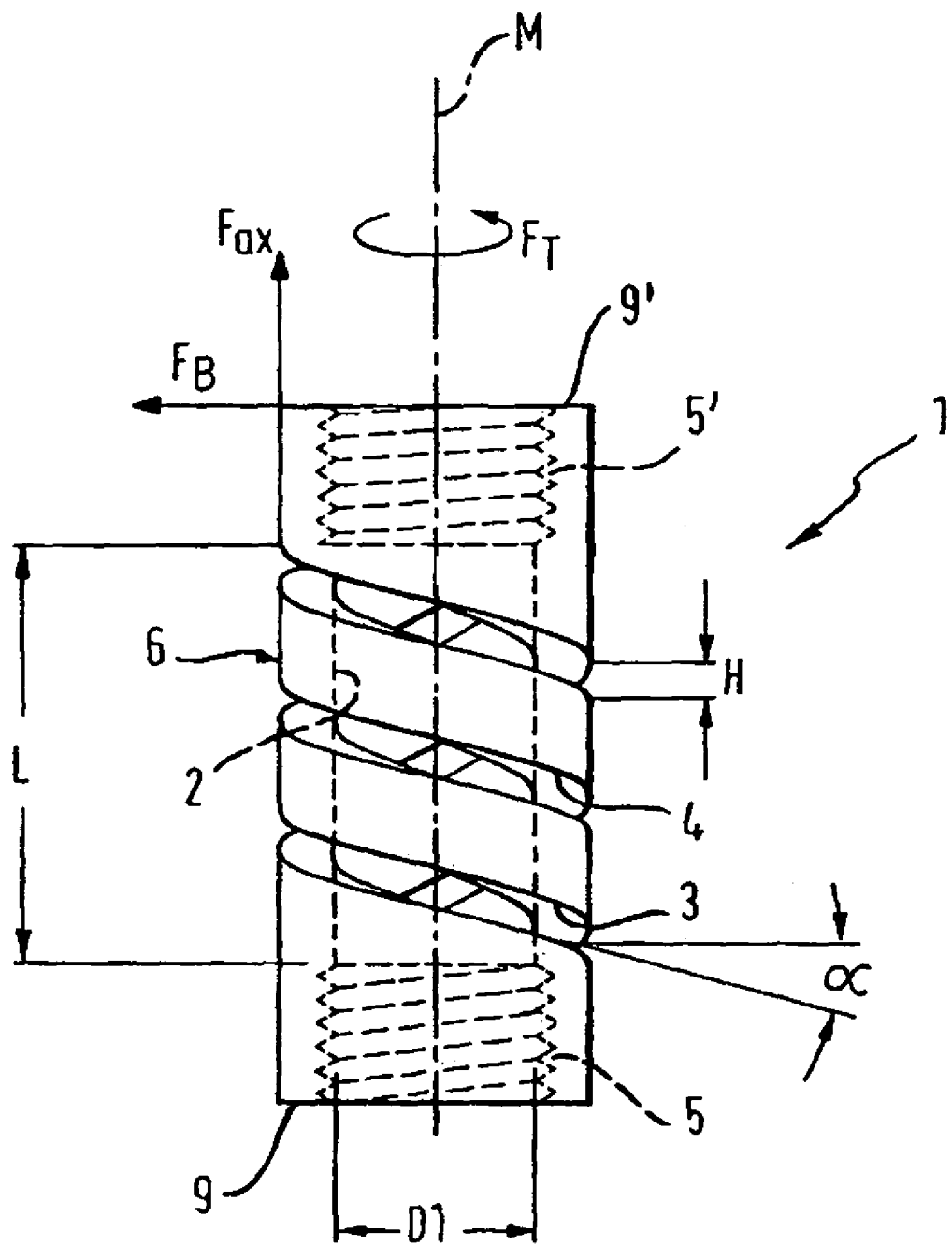
FIG. 1 is an elevational view of an elastic element according to a first embodiment.

Various embodiments of the invention are illustrated in FIGS. 1-11 and described herein. Elements of the various embodiments that are substantially identical will be referred to with the reference numerals.

Figure 2A:
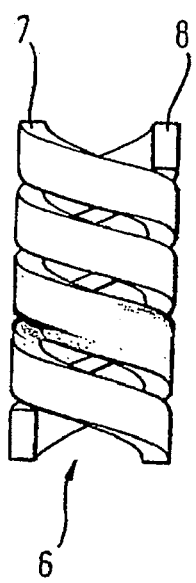
FIG. 2a is an elevational view of a double helical spring of the elastic element of FIG. 1.
Figure 2B:
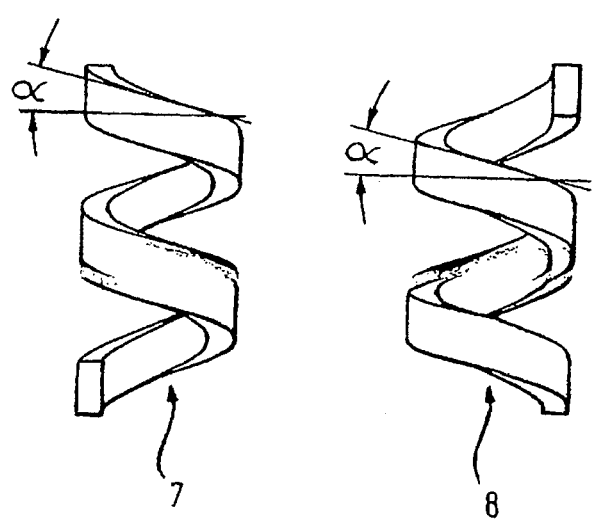
FIG. 2b is an exploded view of the double helical spring of the elastic element of FIG. 1.

FIGS. 1-2b show an elastic element 1 according to a first embodiment of the invention. The elastic element 1 may be made, for example, from a bio-compatible material, such as titanium. Examples of other bio-compatible materials include stainless steel, titanium alloys, nickel-titanium alloys, nitinol, chrome alloy, cobalt chrome alloys, shape memory alloys, materials with super elastic properties, carbon reinforced composites, silicone, polyurethane, polyester, polyether, polyalkene, polyethylene, polyamide, poly(vinyl) fluoride, polyetheretherketone (PEEK), polytetrafluoroethylene (PTFE) and shape memory materials or alloys, such as nickel titanium or nitinol. As shown in FIG. 1, the elastic element 1 is a substantially hollow cylindrical member with an outer wall and a continuous coaxial bore 2. The coaxial bore 2 extends from a first end 9 to a second end 9' of the elastic element 1 and has a diameter D1. A first helical recess 3 is formed in the outer wall in a direction of a central axis M of the cylindrical member. The first helical recess 3 has a height H and opens into the coaxial bore 2 in a radial direction. The first helical recess 3 is formed at a predetermined angle a and extends over a predetermined length L of the outer wall. A second helical recess 4 is formed in the outer wall in-between the first helical recess 3 in the direction of the central axis M of the cylindrical member. The second helical recess 4 is formed at substantially the same angle a and extends over substantially the same length L of the outer wall as the first helical recess 3. The second helical recess 4 opens into the coaxial bore 2 in the radial direction.

First and second internal threads 5, 5' are formed at the first and second ends 9, 9', respectively, of the elastic element 1. The first and second internal threads 5, 5' extend over a predetermined length in an axial direction. The first and second internal threads 5, 5' do not overlap or extend into the first and second helical recesses 3, 4 formed in the outer wall. The elastic element 1 has an outer diameter, which is selected according to the desired use thereof. The length L of the first and second helical recesses 3, 4 in the direction of the central axis M of the cylindrical member, the height H of the first and second recesses 3, 4, the angle a of the helices along which the first and second helical recesses 3, 4 are formed, and the diameter D1 of the coaxial bore 2 is selected to provide a desired stiffness to the elastic element 1 with respect to axial forces $F_{ax}$, bending forces $F_B$ and torsional forces $F_T$ acting on the elastic element 1.

As shown in FIGS. 2a-2b, a double helical spring or elastic section 6 consisting of a first helical coil 7 and a second helical coil 8 is formed by the first and second helical recesses 3, 4. Coils of the first helical coil 7 extend between coils of the second helical coil 8. The first and second helical coils 7, 8 are substantially identical and have substantially the same angle a. The coils of the first helical coil 7 are rotated approximately 180 degrees with respect to the coils of the second helical coil 8 around the central axis M, which is common to both the first and second helical coils 6, 7, so that the first and second helical recesses 3, 4 oppose each other. The coils of the first helical coil 7 therefore run midway between the coils of the second helical coil 8 and vice versa. It will be appreciated by those skilled in the art that the elastic member 1 may additionally comprise more than two of the helical coils, wherein coils of each of the helical coils extend in-between coils of adjacent helical coils.

In order to obtain optimal elastic properties in an elastic element (not shown) with a single helical spring (not shown) having a predetermined length, the angle of the helices of the single helical spring (not shown) must be formed to have at least one whole turn. In the double helical spring 6 shown in FIGS. 2a-2b, however, the first helical coil 7 and the second helical coil 8 require less than one whole turn to obtain optimal elastic properties even though the double helical spring 6 has the same predetermined length as the single helical spring (not shown). Unlike the angle of the helices of the single helical spring (not shown), the angle a of the helices of the double helical spring 6 may therefore be increased to increase the flexural strength of the elastic element 1. Additionally, the elastic element 1 may be formed, for example, to have an ovular cross-section or to be wasted such that the elastic element 1 has a flexural strength which is dependent on direction. The elastic element 1 therefore has a high flexural strength and a short length such that the elastic element 1 may be handled easily while at the same time providing a high operational reliability. Additionally, the elastic element 1 may be combined with other elements in various different ways to be a dynamic stabilization device for vertebrae or bones.

Figure 3:
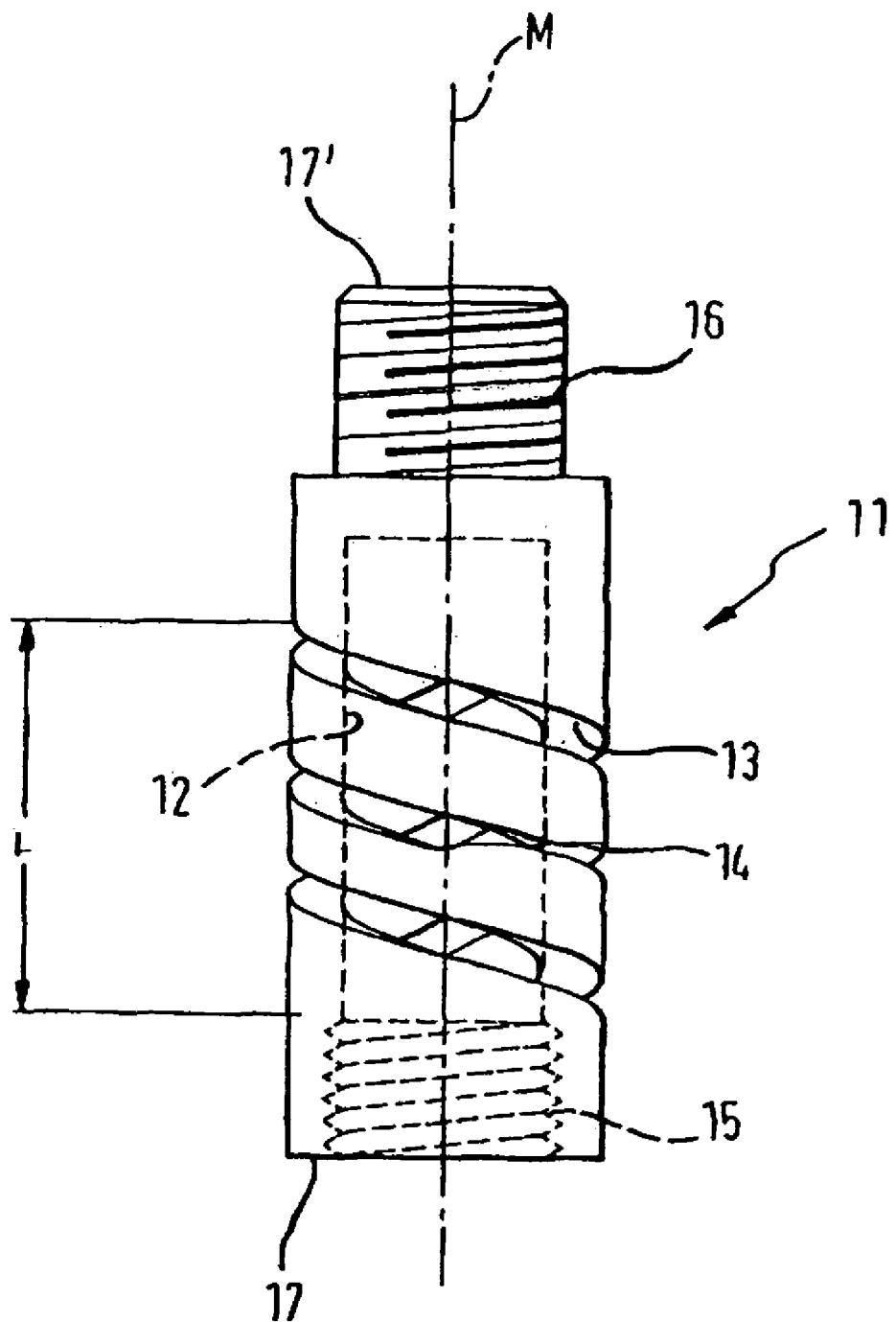
FIG. 3 is an elevational view of an elastic element according to a second embodiment.

FIG. 3 shows an elastic element 11 according to a second embodiment of the invention. The elastic element 11 is a substantially hollow cylindrical member having first and second helical recesses 13, 14 formed in an outer wall thereof to form a double helical spring or elastic section. The double helical spring is formed in a similar fashion to the first embodiment. The elastic element 11 of the second embodiment differs from the first embodiment in that the elastic element 11 has a coaxial bore 12 that extends partially through the cylindrical member. The coaxial bore 12 extends from a first end 17 over the length L of the double helical spring and is coaxial with the central axis M of the cylindrical member. Internal threads 15 are provided in the coaxial bore 12 adjacent to the first end 17. At a second end 17', which opposes the first end 17, the elastic element 11 is provided with a cylindrical projection 16. The cylindrical projection 16 has external threads. Alternatively, the coaxial bore 12 may have a diameter smaller than an outer diameter of the cylindrical projection 16 and may extend through the entire cylindrical member.

Figure 4A:
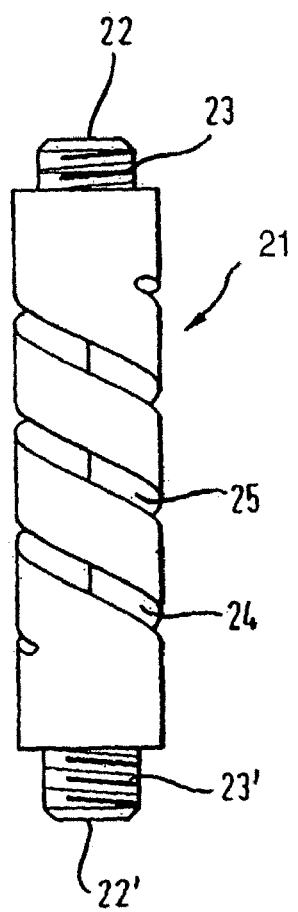
FIG. 4a is an elevational view of an elastic element according to a third embodiment.
Figure 4B:
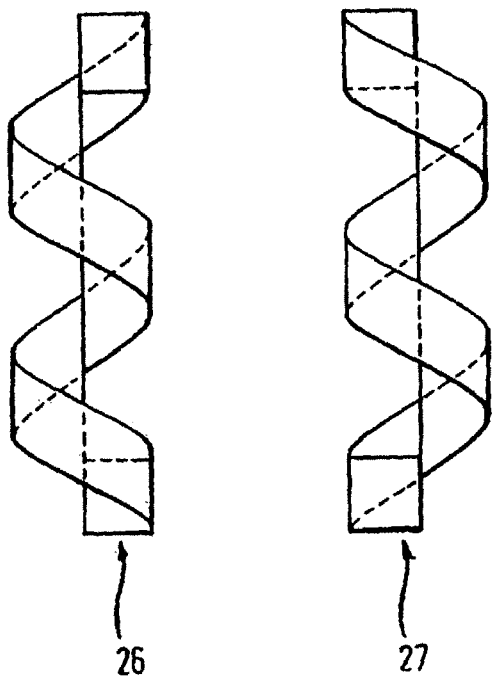

FIGS. 4a-4b show an elastic element 21 according to a third embodiment of the invention. The elastic element 21 is a substantially cylindrical member having first and second helical recesses 24, 25 formed in an outer wall thereof to form a double helical spring or elastic section consisting of a first helical coil 26 and a second helical coil 27. The double helical spring is formed similar to the first and second embodiments. The elastic element 21 of the third embodiment differs from the first and second embodiments in that the elastic element 21 does not have a bore coaxial with the central axis M of the cylindrical member. The elastic member 21 has a first end 22 and a second end 22'. The first and second ends 22, 22' have first and second cylindrical projections 23, 23', respectively. The first and second cylindrical projections 23, 23' have external threads.

Figure 5A:
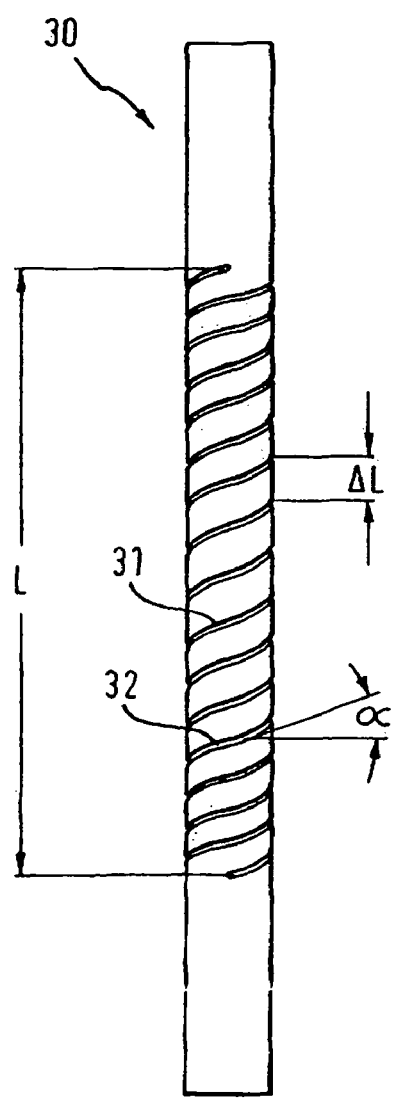
FIG. 5a is an elastic element with a double helical coil section according to a fourth embodiment of the invention.
Figure 5B:
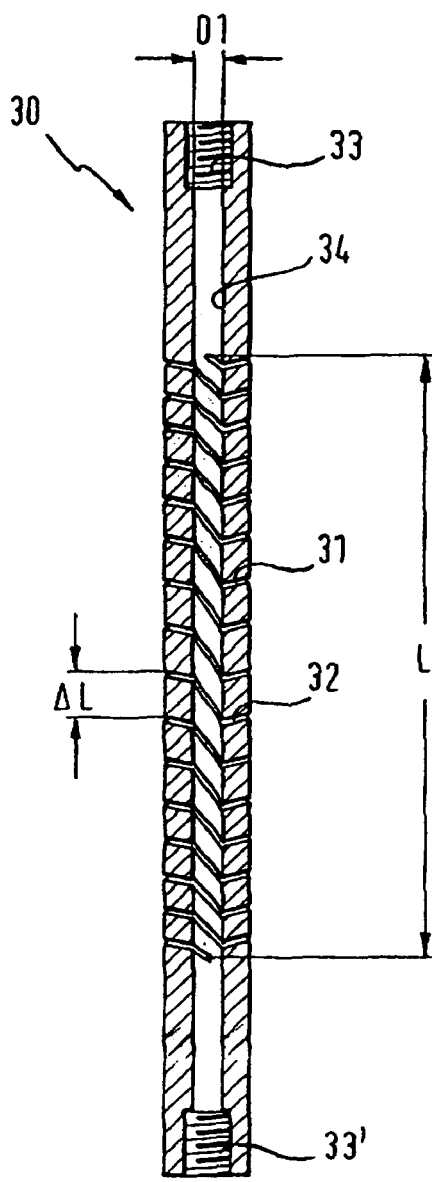
Figure 6:
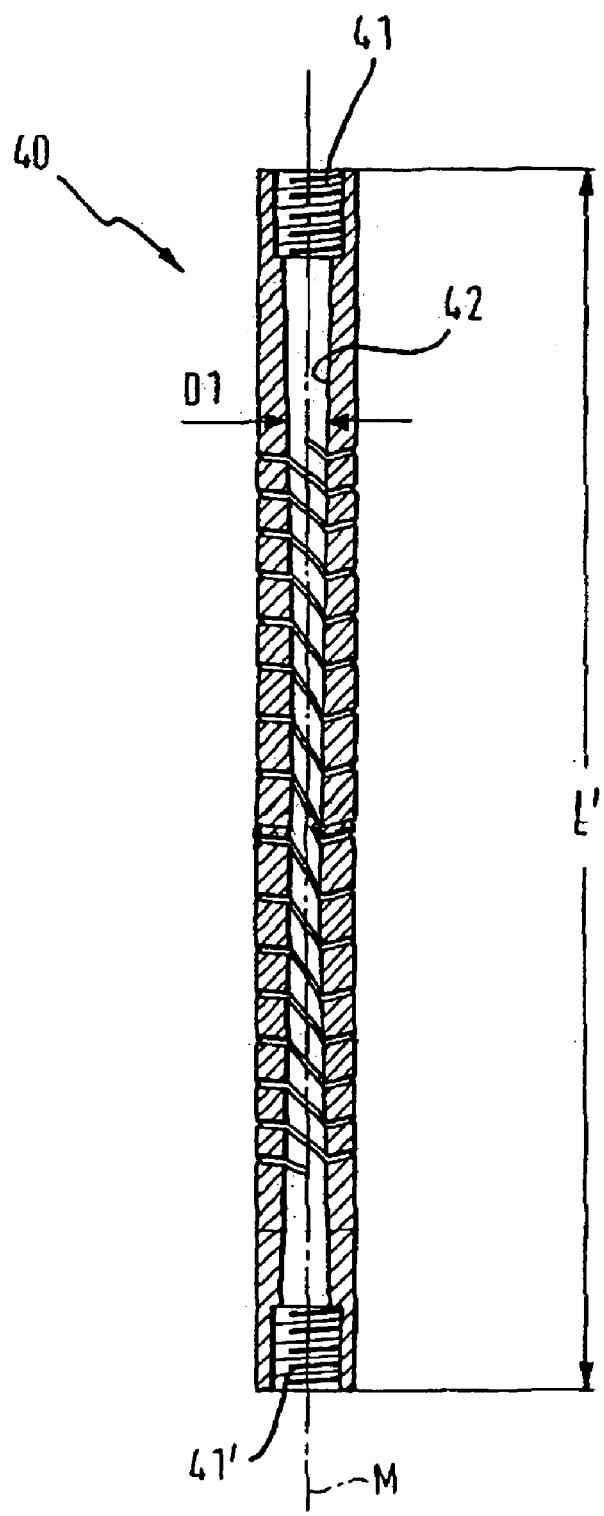
FIG. 6 is a sectional view of an elastic element having a double helical coil section according to a fifth embodiment of the invention.

An elastic element according to a fourth embodiment is shown in FIG. 5a. FIG. 5b is a sectional view of the elastic element of FIG. 5a. The elastic element 30 according to the fourth embodiment differs from the elastic element according to the first embodiment in that the pitch a of the recesses 31, 32 which form the double helical coil is not constant but varies over the length L of the double helical coil of the elastic element 30. The pitch a varies in such a way that the distance L of the recesses 31, 32 increases from the free ends of the elastic element 30 towards the middle. Accordingly, the bending stiffness of the elastic element 30 varies and increases with increasing distance L of the recesses 31, 32. By varying the pitch of the recesses along the central axis of the elastic element, it is possible to achieve a particular stiffness at a particular position. Similar to the elastic element of the first embodiment, the elastic element 30 according to the fourth embodiment has coaxial bore 34 having an inner diameter D1 and inner threads 33, 33' extending a predetermined length from the free end, respectively. FIG. 6 shows sectional view of an elastic element according to a fifth embodiment.

The elastic element according to the fifth embodiment differs from the elastic element 30 according to the fourth embodiment in that the inner diameter D1 of the continuous coaxial bore 42 is not constant but varies of the length L' of the elastic element 40. The inner diameter D1 of the bore 42 varies in such a way that it decreases from the free ends towards the middle of the elastic element 40. Accordingly, the final stiffness of the elastic element 40 varies and increases with decreasing inner diameter D1. By varying the inner diameter of the coaxial bore, the stiffness of the elastic element 40 can be varied at different positions.

Similar to the fourth embodiment the elastic element 40 includes a section with an inner thread 41, 41' having a predetermined length adjacent to each of its free end, respectively.

Figure 7A:
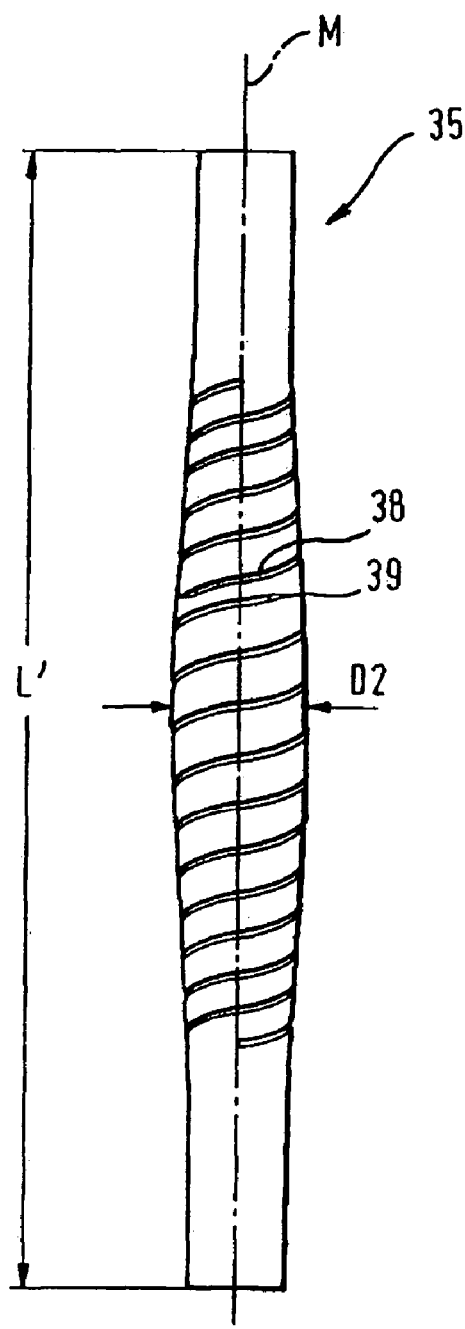
FIG. 7a is an elastic element having a double helical coil section according to a sixth embodiment of the invention.
Figure 7B:
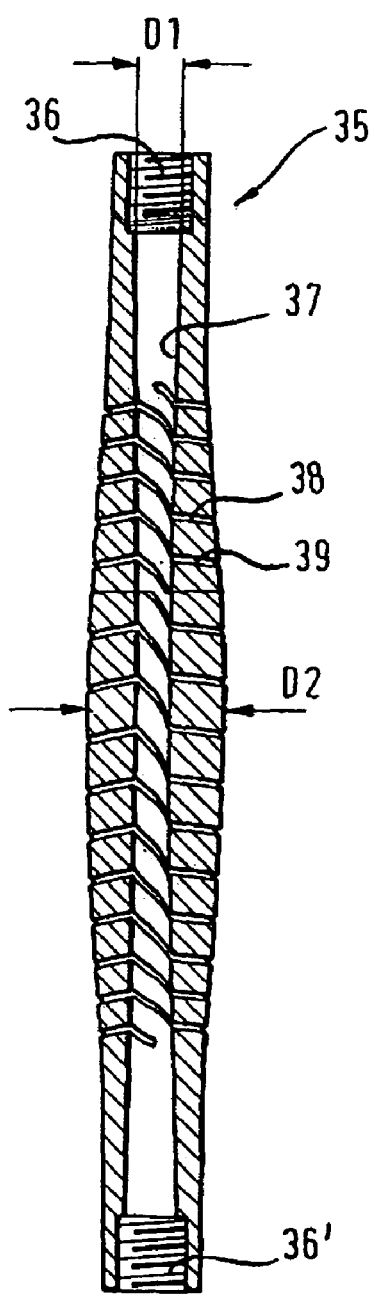

In FIG. 7a an elastic element according to a sixth embodiment is shown. FIG. 7b is a sectional view of the elastic element of FIG. 7a.

The elastic element 35 according to the sixth embodiment differs from that of the fifth embodiment in that the outer diameter D2 of the elastic element 35 is not constant but varies over the length L' of the elastic element 35. The outer diameter D2 varies in such a way that it increases from the free ends towards the middle of the elastic element 35. Accordingly, the bending stiffness of the elastic element 35 varies and increases with increasing outer diameter. Therefore, a position with a desired bending stiffness can be obtained by adjusting the outer diameter of the elastic element.

Similar to the fourth embodiment the elastic element 35 has adjacent to its free ends a section with an inner thread 36, 36' of a predetermined length, respectively, and a continuous coaxial bore 37 with an inner diameter D1. Recesses 38 and 39 to form the double helical coil are formed like in the other embodiments.

In the fourth to sixth embodiments of the instant invention, the bending stiffness of the elastic element increases from the free ends towards the middle of the elastic element. However, by appropriate selection of the pitch a of the recesses, the outer diameter D2 of the elastic element and the inner diameter D1 of the coaxial bore, the bending stiffness can be adjusted to have a desired stiffness at a particular position along the length L, L' of the double helical coil of the elastic element.

FIG. 8a illustrates a first example of an application of the elastic element 1. As shown in FIG. 8a, the elastic element 1 may form a portion of a rod 50, which may be used, for example, to connect pedicle screws (not shown) at a spinal column (not shown). The rod 50 in the illustrated embodiment consists of the elastic element 1 and first and second end portions 51, 51'. The first and second end portions 51, 51' each have a cylindrical projection (not shown) with external threads (not shown) that cooperates with the first and second internal threads 5, 5', respectively, of the elastic element 1, shown in FIG. 1. Alternatively, an external nut (not shown) or other attachment member may be used to fix the elastic element 1 to the first and second end portions 51, 51'. In the illustrated embodiment, the first and second end portions 51, 51' and the elastic element 1 have approximately the same outer diameter. The first and second end portions 51, 51' have a length that may be selected independently from the length L of the elastic element 1, which is shown in FIG. 1. The length of the first and second end portions 51, 51' and the length L of the elastic element 1 selected depends on a desired end application. Because the rod 50 is formed with the elastic element 1, the rod 50 can absorb compression forces, extension forces, bending forces and torsional forces to a predetermined extent by means of the elastic properties of the elastic element 1.

Figure 8B:
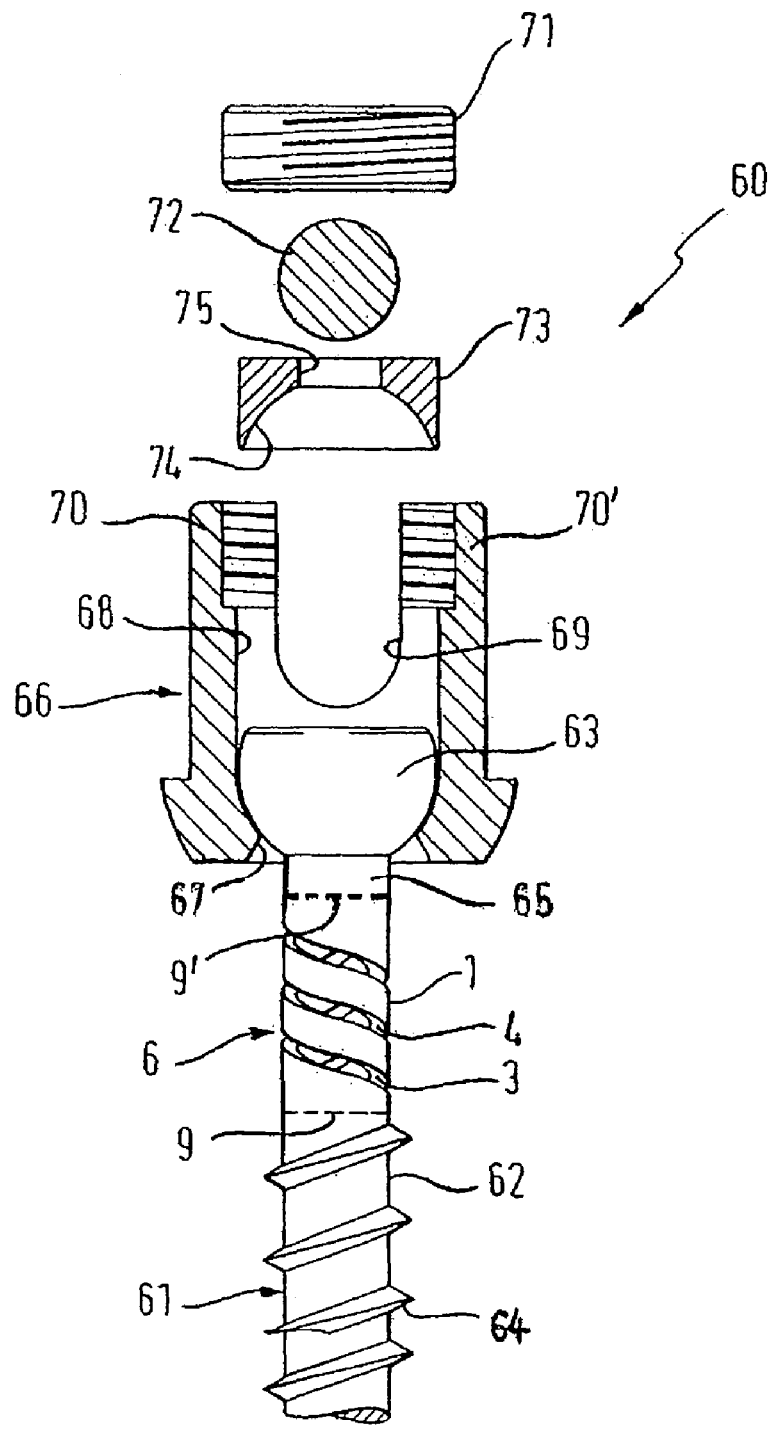
FIG. 8b is a partial sectional exploded view of a polyaxial bone screw comprising the elastic element of FIG. 1.

FIG. 8b illustrates a second example of an application of the elastic element 1. As shown in FIG. 8b, the elastic element 1 may form a portion of a bone anchoring element, such as a polyaxial bone screw 60. The polyaxial bone screw 60 in the illustrated embodiment includes a screw 61 with a shaft 62 and a head 63. The shaft 62 has a tip (not shown) and includes bone threads 64 for screwing into a bone (not shown) and. A cylindrical projection (not shown) extends from the shaft 62 on a side opposite from the tip (not shown) and has external threads (not shown) that cooperate with the internal threads 5 of the elastic element 1, which are shown in FIG. 1. As shown in FIG. 8b, the head 63 has a cylindrical section 65 adjacent thereto. A cylindrical projection (not shown) extends from the cylindrical section 65 and has external threads (not shown) that cooperate with the internal threads 5' of the spring element 1, which are shown in FIG. 1.

As shown in FIG. 8b, the screw 61 is pivotally held in a receiving member 66 in an unloaded state. The receiving member 66 is substantially cylindrical and has a first receiving member bore 67 and a second receiving member bore 68. The first receiving member bore 67 is provided at a first end of the receiving member 66. The first receiving member bore 67 is substantially axially symmetrical and has a diameter larger than a diameter of the shaft 62 but smaller than a diameter of the head 63. The second receiving member bore 68 is substantially coaxial and opens at a second end of the receiving member 66 opposite the first end. The second receiving member bore 68 has a diameter large enough that the shaft 62 of the screw 61 may be guided through the second end and the second receiving member bore 68 until the head 63 abuts an edge of the first receiving member bore 67. The receiving member 66 has a substantially U-shaped recess 69, which extends from the second end towards the first end. The substantially U-shaped recess 69 forms first and second legs 70, 70' with free ends. In a region adjacent to the free ends, the first and second legs 70, 70' have internal threads, which cooperate with corresponding external threads of a securing element 71 that fixes a rod 72 in the receiving member 66.

A pressure element 73 that is provided for fixation of the head 63 in the receiving member 66 has a concave recess 74 on a side facing the head 63. The concave recess 74 has a radius substantially identical to a radius of the head 63. The pressure element 73 has an outer diameter selected so that the pressure element 73 can be inserted into the receiving member 66 and can slide towards the head 63. The pressure element 73 has a coaxial pressure element bore 75 for providing access to a tool receiving recess (not shown) in the head 63.

During assembly, the cylindrical projection (not shown) of the shaft 62 is screwed into the internal threads 5 of the elastic element 1 and the cylindrical projection (not shown) of the cylindrical section 65 of the head 63 is screwed into the internal threads 5' of the elastic element 1 to form the screw 61. The shaft 62 of the screw 61 is then inserted into the second end of the receiving member 66 and guided through the second receiving member bore 68 until the head 63 abuts the edge of the first receiving member bore 67. The pressure element 73 is inserted into the second receiving member bore 68 so that the concave recess 74 is positioned adjacent to the head 63. The screw 61 is screwed into a bone (not shown) or vertebra (not shown). The rod 72 is inserted into the receiving member 66 and is arranged between the first and second legs 70, 70'. The angular position of the screw 61 relative to the receiving member 66 is then adjusted and fixed with the securing element 71.

Because the screw 61 is formed with the elastic element 1, the screw 61 may be diverted from the angular position by a limited extent. Additionally, if the elastic element 1 protrudes at least partially above a surface of the bone (not shown), the elastic element 1 can absorb compression forces, extension forces, bending forces and torsional forces because of the elastic properties of the elastic element 1. If the elastic element 1 does not at least partially protrude above the surface of the bone (not shown), the screw 61 can still slightly yield, when the bone (not shown) or vertebra (not shown) moves such that the occurrence of unfavorable stress is avoided.

Figure 8C:
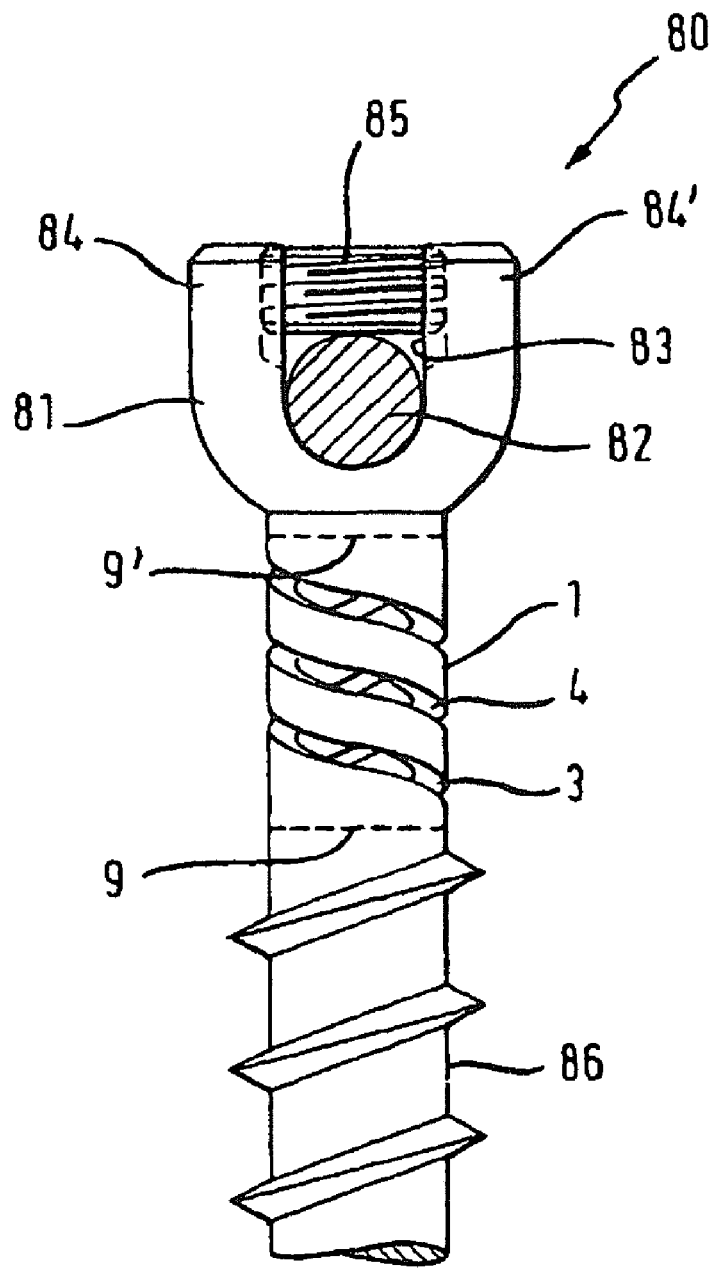
FIG. 8c is a partial sectional view of a monoaxial screw comprising the elastic element of FIG. 1.

FIG. 8c illustrates a third example of an application of the elastic element 1. As shown in FIG. 8c, the elastic element 1 may form a portion of a bone anchoring element, such as a monoaxial screw 80. The monoaxial screw 80 in the illustrated embodiment consists of a head formed as a receiving member 81 and a shaft 86. The receiving member 81 has a substantially U-shaped recess 83 formed at a first end thereof. First and second legs 84, 84' are formed by the U-shaped recess 83. The first and second legs 84, 84' receive a rod 82 therebetween. Internal threads (not shown) that correspond to external threads on securing member 85 are formed on inside surfaces of the first and second legs 84, 84'. The rod 82 is clamped between a bottom surface of the U-shaped recess 83 and the securing member 85 when the securing member 85 is engaged with the internal threads (not shown). A cylindrical projection (not shown) extends from a second end of the receiving member 81 opposite from the first end. The cylindrical projection (not shown) has external threads (not shown) that correspond to the internal threads 5' of the elastic element 1, which are shown in FIG. 1. The shaft 86 is similar to the shaft 62 previously described and has a cylindrical projection (not shown) extending therefrom with external threads (not shown) that corresponds to the internal threads 5 of the elastic element 1, which are shown in FIG. 1.

During assembly, the cylindrical projection (not shown) of the shaft 86 is screwed into the internal threads 5 of the elastic element 1 and the cylindrical projection (not shown) of the receiving member 81 is screwed into the internal threads 5' of the elastic element 1 to form the monoaxial screw 80. The monoaxial screw 80 is screwed into a bone (not shown) or vertebra (not shown). The U-shaped recess 83 is aligned and the rod 82 is inserted into the receiving member 81 and is arranged between the first and second legs 84, 84". The rod 82 is then fixed by the securing member 85.

Figure 8D:
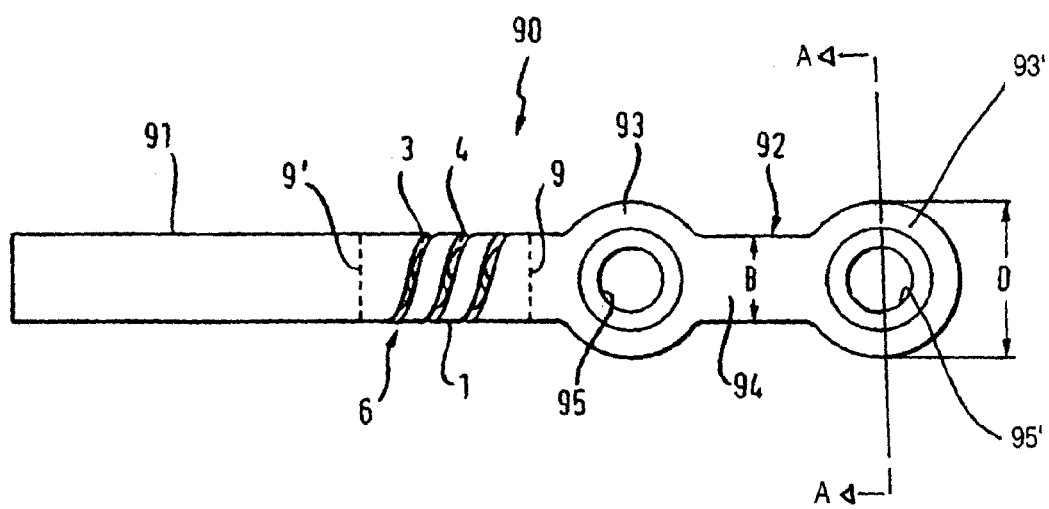
FIG. 8d is a plan view of a connecting element comprising the elastic element of FIG. 1.
Figure 8E:
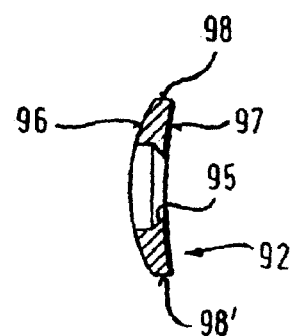
FIG. 8e is a sectional view taken along line A-A of FIG. 8d.

FIGS. 8d-8e illustrate a fourth example of an application of the elastic element 1. As shown in FIG. 8d, the elastic element 1 may form a portion of a connecting element 90. The connecting element 90 in the illustrated embodiment consists of a rod 91 and a plate 92. The rod 91 has a cylindrical projection (not shown) with external threads that correspond to the internal threads 5 of the elastic element 1, which are shown in FIG. 1. A cylindrical projection (not shown) extends from the plate 92 and has external threads (not shown) corresponding to the internal threads 5' of the elastic element 1, which are shown in FIG. 1. As shown in FIG. 8d, the plate 92 has a first section 93 and a second section 93' connected by a bridge 94. The first and second sections 93, 93' are substantially circular from a top view. The bridge 94 has a width B smaller than a diameter D of the first and second sections 93, 93'. The first and second sections 93, 93' each have a screw receiving bore 95, 95', respectively, formed coaxially with the first and second sections 93, 93'. The screw receiving bores 95, 95' have a shape adapted for the reception of countersunk screws (not shown). As shown in FIG. 8e, a first side 96 of the plate 92 has a convex curvature and a second side 97 of the plate 92 has a concave curvature for abutting a surface of a bone (not shown). Due to the different curvatures of the first and second sides 96, 97, the plate 92 tapers towards lateral edges 98, 98'. The plate 92 is, therefore, stable and compact.

Modifications of the rod 50, the polyaxial bone screw 60, the monoaxial screw 80, and the connecting element 90, shown in FIGS. 8a-8e are also possible. For example, the elastic element 1 in the rod 50, the polyaxial bone screw 60, the monoaxial screw 80, and the connecting element 90 is illustrated as being a separate element that requires connection therewith. Alternatively, the elastic element 1 may be integrally formed with the polyaxial bone screw 60, the monoaxial screw 80, and the connecting element 90 or press-fit thereto.

Figure 9:
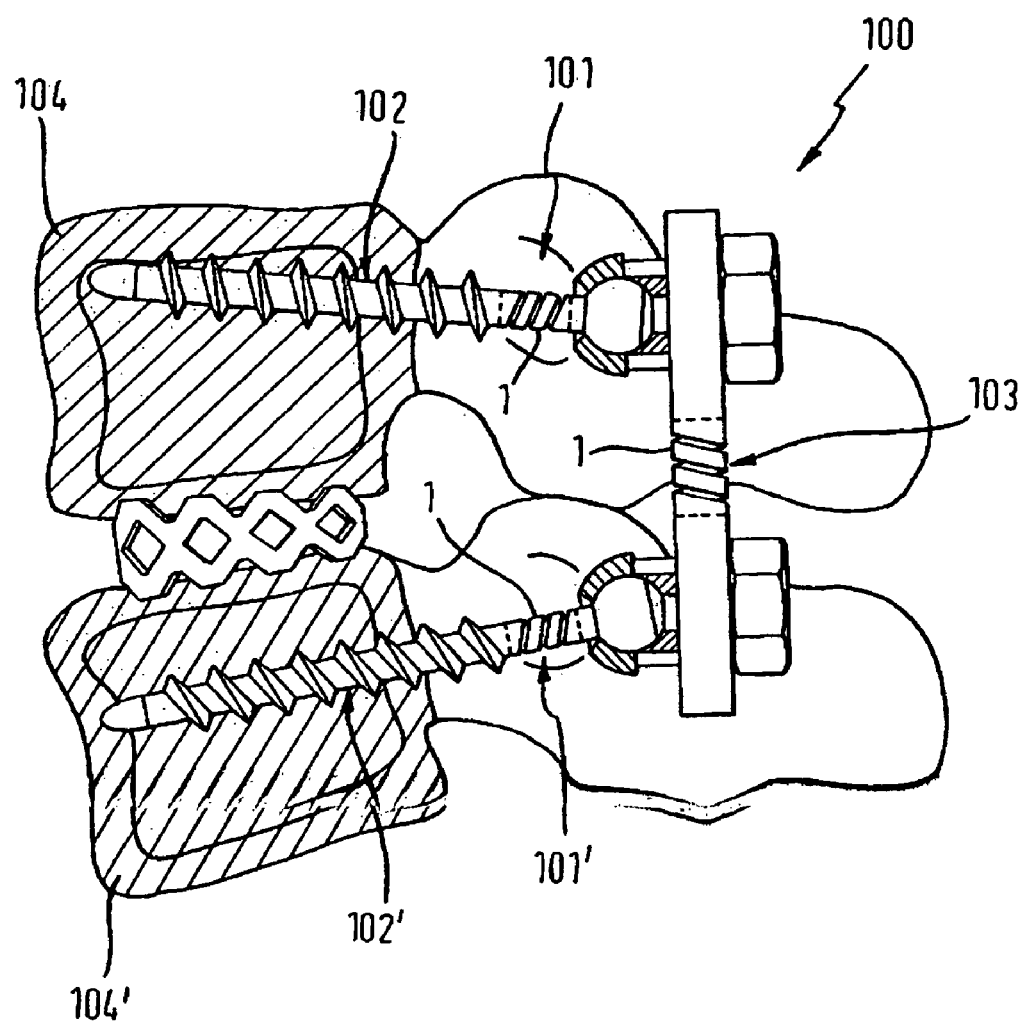
FIG. 9 is a partial sectional view of a stabilization device comprising several of the elastic elements of FIG. 1.

FIG. 9 illustrates a fifth example of an application of the elastic element 1. As shown in FIG. 9, the elastic element 1 may form a portion of a stabilization device 100 that is used, for example, in spinal columns. The stabilization device 100 in the illustrated embodiment consists of first and second bone anchoring elements 101, 101', respectively, connected by a rod 103. Each of the first and second bone anchoring elements 101, 101' has a screw 102, 102', respectively, formed with an elastic element 1. The rod 103 is also formed with an elastic element 1. Each of the screws 102, 102' is screwed into a vertebra 104, 104' so that a dynamic stabilization is established between the vertebrae 104, 104' and the stabilization device 100. Because the rod 103 and the screws 102, 102' are made of several elements, the stabilization device 100 has various properties by the combination of only a few basic elements. The stabilization device 100 is not limited to the embodiment illustrated and depending on a desired application thereof, it is possible, for example, to provide only the rod 103 with the elastic element 1.

A method of manufacturing the elastic element 1 by wire electrical discharge machining (EDM) is shown in FIGS. 10a-10c. As shown in FIG. 10a, a first bore 110 is formed in a solid cylinder 112 of a biocompatible material, such as titanium, perpendicular to a central axis M' of the cylinder 112. The first bore 110 extends through the whole cylinder 112. A second bore 111 is formed coaxial with the central axis M' of the cylinder 112 so that the cylinder 112 is made hollow. The order of forming the first and second bores 110, 111 is arbitrary and may be varied according to a desired manufacturing process. A wire 113 for wire EDM is guided through the first bore 110 in a direction indicated by arrow P.

As shown in FIG. 10b, wire EDM is performed by moving the cylinder 112 in a direction indicated by arrow X along the central axis M'. The cylinder 112 is moved at a constant feed rate relative to the wire 113 and is simultaneously rotated around the central axis M' in a direction indicated by arrow R with a constant angular velocity. Only relative movement of the wire 113 relative to the cylinder 112 is relevant. Accordingly, either the wire 113 or the cylinder 112 may be fixed during the wire EDM. As the cylinder 112 is rotated, first and second helical recesses 114, 115 are formed.

As shown in FIG. 10c, after the first and second helical recesses 114, 115 have been formed over a predetermined length of the cylinder 112 along the central axis M', the rotation of the cylinder 112 is stopped. FIG. 10c shows the elastic element 1 shortly before completion of the wire EDM. The wire EDM thereby simultaneously forms in the outer wall of the cylinder 112, first and second helical recesses 114, 115 having approximately identical angles, which open in a radial direction into the second bore 111.

Figure 11:
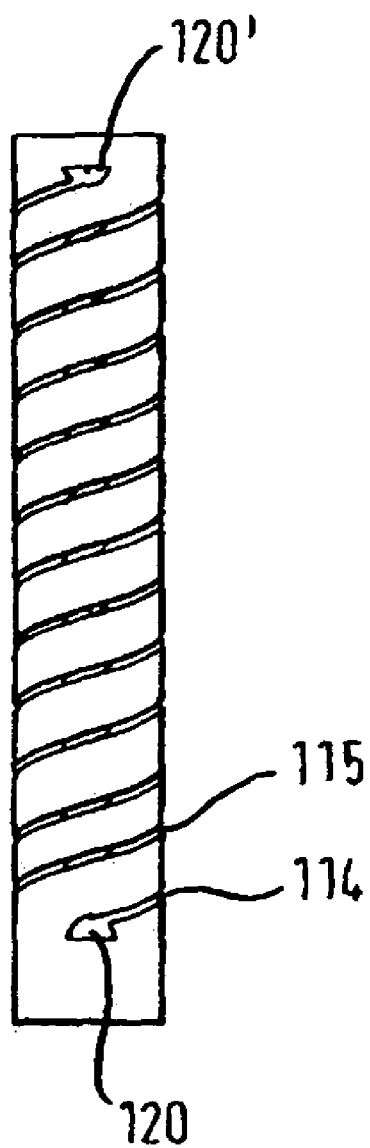
FIG. 11 is a schematic illustration of a method of manufacturing the elastic element of FIG. 1.

As shown in FIG. 11, a first run-out 120 may be formed at a beginning of the wire EDM and at a second run-out 120' may be formed at an end of the wire EDM. The first and second run-outs 120 and 120' have a configuration by which load peaks can be minimized in the material at a transition from the elastic section to the rigid section during operation. The first and second run-outs 120, 120' may have, for example, a semi-circular configuration. The first and second run-outs 120, 120' advantageously may be made in one common manufacturing step. Additionally, unlike during the manufacture of a single helical spring (not shown), during the manufacture of the elastic element 1, switching between each axis of the wire EDM machine is not necessary. Internal threads are then formed along the central axis M' in end sections of the second bore 111 adjacent to the first and second ends.

Alternatively, the elastic element 1 may be milled. A first helical recess is milled along a first helix of a central axis of a solid cylinder formed of a bio-compatible material, such as titanium, having a predetermined outer diameter. The first helical recess is formed collinear with the central axis of the cylinder by a side mill. A second helical recess is milled along a second helix of the central axis such that coils of the second helical recess run between coils of the first helix. A bore is formed along the central axis of the cylinder over the whole length of the cylinder so that the first and second helical recesses communicate with the bore. The first and second helical recesses have first and second run-outs, respectively. The first and second run-outs of the first and second helical recesses at a transition between the first and second helices and end sections of the cylinder have a large influence on the stability of the elastic element 1. The first and second run-outs of the first and second helixes at both of the end sections are reworked by an end mill so that sharp edges on an internal surface of the bore are removed. The first and second run-outs are milled by the end mill at an angle that is tangential relative to a helical line. The part is then chamfered on an inside and on an outside. Internal threads are then formed along the central axis in the end sections of the bore adjacent to first and second ends of the cylinder.

Further alternative methods for manufacturing the elastic element 1 are, for example, laser milling or hydro milling. These methods are performed similar to the wire EDM method, but instead of simultaneously forming the first and second helical recesses by a wire, a laser beam or a water beam is used. Additionally, instead of forming at least one of the internal threads, a cylindrical projection with external threads may be formed at a beginning of any one of the manufacturing methods by a lathe. In this instance, the bore has a diameter smaller than a diameter of the cylindrical projection. The spring element 1 may also be formed without the bore.

The embodiments described above and shown herein are illustrative and not restrictive. The scope of the invention is indicated by the claims, including all equivalents, rather than by the foregoing description and attached drawings. The invention may be embodied in other specific forms without departing from the spirit and scope of the invention.

We claim:

1. An implantable element for use in a bone anchoring element having a shaft, the implantable element comprising:
a multi-part piece with at least a rigid cylindrical section and an elastic section as separate members, the elastic section having a first end, a second end opposite to the first end, and a central axis extending from the first end to the second end, the elastic section being configured to be connected with the rigid cylindrical section at one of the first and second ends, wherein the elastic section forms part of the shaft of the bone anchoring element;
the elastic section including at least a first helical coil and a second helical coil, the first and second helical coils being arranged coaxially and extending along a same length of the central axis, an inner radius of the first helical coil less than an outer radius of the second helical coil and an outer radius of the first helical coil greater than an inner radius of the second helical coil, each radius measured from the central axis, so that the first helical coil extends at least in a portion in a helical recess of the second helical coil in a direction of the central axis;
wherein the first helical coil and the second helical coil rotate in the same direction relative to the central axis; and
wherein the helical recess of the second helical coil is defined by a helical space extending along the central axis between adjacent windings of the second helical coil.

2. The elastic element of claim 1, wherein the first and second helical coils are substantially identical.

3. The elastic element of claim 1, wherein the elastic element is formed from a biocompatible material.

4. The elastic element of claim 1, wherein at least one of the first and second ends are provided with internal threads.

5. The elastic element of claim 1, wherein at least one of the first and second ends is provided with a cylindrical projection having external threads.

6. The elastic element of claim 1, wherein the elastic section has a coaxial bore that extends along the central axis through a portion of the elastic section.

7. The elastic element of claim 6, wherein a diameter of the coaxial bore varies over the length of the portion of the elastic section.

8. The elastic element of claim 1, wherein the elastic section has a coaxial bore that extends along the central axis through the entire elastic section.

9. The elastic element of claim 8, wherein a diameter of the coaxial bore varies along the elastic section.

10. The elastic element of claim 1, wherein said first and said second helical coils have a pitch, wherein the pitch of the first and second helical coil is identical.

11. The elastic element of claim 1, wherein said first and said second helical coils have a pitch, wherein the pitch of the first and second helical coils varies over the length of the elastic section.

12. The elastic element of claim 1, wherein the pitch of the first helical coil is different from that of the second helical coil.

13. The elastic element of claim 1, wherein an outer diameter of the elastic section varies over a length of the elastic section.

14. The elastic element of claim 1, wherein the first helical coil and the second helical coil have the same stiffness.

15. The implantable element of claim 1, wherein at least one of the first and second ends is a threaded end with threads surrounding the central axis.

16. The implantable element of claim 1, wherein the elastic section further includes a coaxial bore that extends along the central axis through the at least one of the first and second ends, wherein at least a portion of the coaxial bore that extends through the at least one of the first and second ends includes internal threads for forming a threaded end of the elastic section.

17. An implantable stabilization device for bones or vertebrae, comprising:
  a bone anchoring element formed as a multi-part piece with at least a rigid cylindrical section and an elastic section as separate members, the elastic section having a first end and a second end opposite to the first end, and a central axis extending from the first end to the second end, the elastic section being configured to be connected with the rigid cylindrical section at one of the first and second ends, the elastic section forming part of a shaft of the bone anchoring element, the elastic section including at least a first helical coil and a second helical coil, the first and second helical coils being arranged coaxially and extending along a same length of the central axis, an inner radius of the first helical coil less than an outer radius of the second helical coil and an outer radius of the first helical coil greater than an inner radius of the second helical coil, each radius measured from the central axis, so that the first helical coil extends at least in a portion in a helical recess of the second helical coil in a direction of the central axis, wherein the first helical coil and the second helical coil rotate in the same direction relative to the central axis, and wherein the helical recess of the second helical coil is defined by a helical space extending along the central axis between adjacent windings of the second helical coil.

18. A method of manufacturing an implantable elastic element for a stabilization device for bones or vertebrae, comprising the steps of:
  providing a substantially cylindrical body having a first end, a second end opposite to the first end, and a central axis extending from the first end to the second end; and
  forming an elastic section between the first end and the second end with at least first and second helical coils so that the elastic section has a particular flexural strength by selecting a first angle of helices of the first helical coil along a central axis to be bigger that a second angle of helices in an implantable elastic element having substantially the same particular flexural strength via only a single helical coil, and forming the second helical coil coaxially with the first helical coil such that the second helical coil extends at least in a portion in a recess defined by the first angle between adjacent helices of the first helical coil;
  wherein the first helical coil and the second helical coil rotate in the same direction relative to the central axis.

19. The method of claim 18, wherein the first and second helical coils are formed by wire electrical discharge machining or milling.

20. The method of claim 18, further comprising the step of forming a bore coaxial with the central axis of the cylindrical member.

21. The method of claim 18, further comprising the step of forming a run-out proximate at least one end of the cylindrical member.

22. The method of claim 18, wherein the first and second helical coils are formed with approximately the same pitch angle.

23. The method of claim 18, wherein the first and second helical coils are foamed simultaneously.

24. An implantable element for use in a bone anchoring element having a shaft and a head with a cylindrical member, the implantable element comprising:
  a multi-part piece with at least a rigid cylindrical section and an elastic section as separate members, the elastic section having a first end, a second end opposite to the first end, and a central axis extending from the first end to the second end, wherein the elastic section forms part of the shaft of the bone anchoring element;
  the elastic section including at least a first helical coil and a second helical coil, the first and second helical coils being arranged coaxially and extending along a same length of the central axis, an inner radius of the first helical coil less than an outer radius of the second helical coil and an outer radius of the first helical coil greater than an inner radius of the second helical coil, each radius measured from the central axis, so that the first helical coil extends at least in a portion in a helical recess of the second helical coil in a direction of the central axis;
  wherein the first helical coil and the second helical coil rotate in the same direction relative to the central axis;
  wherein the helical recess of the second helical coil is defined by a helical space extending along the central axis between adjacent windings of the second helical coil;
  wherein the first end comprises a threaded portion with threads surrounding the central axis and configured to connect to the rigid cylindrical section; and
  wherein the second end comprises a threaded portion with threads surrounding the central axis and configured to connect to the cylindrical member of the head.

25. The elastic element of claim 24, wherein the threaded portion of at least one of the first and second ends comprises a bore with internal threads.

26. The elastic element of claim 24, wherein the threaded portion of at least one of the first and second ends comprises a cylindrical projection having external threads.

27. A method of stabilizing bones or vertebrae with an implantable element used in a bone anchoring element having a shaft, the implantable element comprising a multi-part piece with at least a rigid cylindrical section and an elastic section as separate members, the elastic section having a first end, a second end opposite to the first end, and a central axis extending from the first end to the second end, wherein the elastic section forms part of the shaft of the bone anchoring element, the elastic section including at least a first helical coil and a second helical coil, the first and second helical coils being arranged coaxially and extending along a same length of the central axis, an inner radius of the first helical coil less than an outer radius of the second helical coil and an outer radius of the first helical coil greater than an inner radius of the second helical coil, each radius measured from the central axis, so that the first helical coil extends at least in a portion in a helical recess of the second helical coil in a direction of the central axis, wherein the first helical coil and the second helical coil rotate in the same direction relative to the central axis, and wherein the helical recess of the second helical coil is defined by a helical space extending along the central axis between adjacent windings of the second helical coil; the method comprising:

coupling the elastic section with the rigid cylindrical section at one of the first and second ends; and
anchoring the shaft into a bone or vertebrae.

* * * * *

UNITED STATES PATENT AND TRADEMARK OFFICE
CERTIFICATE OF CORRECTION

| | | |
|---|---|---|
| PATENT NO. | : 7,833,256 B2 | Page 1 of 1 |
| APPLICATION NO. | : 11/102247 | |
| DATED | : November 16, 2010 | |
| INVENTOR(S) | : Lutz Biedermann et al. | |

It is certified that error appears in the above-identified patent and that said Letters Patent is hereby corrected as shown below:

Column 2, line 30          Delete "recess" Insert -- recesses --

Column 2, line 58          After "element of FIG.7a" Insert -- ; --

Column 2, line 59          After "FIG. 8a is" Delete "a" Insert -- an --

Column 4, line 28          Delete "wasted" Insert -- waisted --

Column 5, line 22          After "shows" Insert -- a --

Column 5, line 37          Delete "end," Insert -- ends, --

Column 6, line 31          Delete "and"

Column 12, line 11, Claim 23          Delete "foamed", Insert -- formed --

Signed and Sealed this
Fourth Day of October, 2011

David J. Kappos
*Director of the United States Patent and Trademark Office*